US012697446B2

(12) United States Patent
Anderson, Jr. et al.

(10) Patent No.: US 12,697,446 B2
(45) Date of Patent: *Aug. 4, 2026

(54) VENTING OF PHARMACEUTICAL DRUG DELIVERY DEVICE FOR AIR FLOW AND HUMIDITY CONTROL

(71) Applicant: Brady Worldwide, Inc., Milwaukee, WI (US)

(72) Inventors: James D. Anderson, Jr., Lexington, KY (US); Michael A. Marra, III, Lexington, KY (US)

(73) Assignee: BRADY WORLDWIDE, INC., Milwaukee, WI (US)

( * ) Notice: Subject to any disclaimer, the term of this patent is extended or adjusted under 35 U.S.C. 154(b) by 395 days.

This patent is subject to a terminal disclaimer.

(21) Appl. No.: 18/581,908

(22) Filed: Feb. 20, 2024

(65) Prior Publication Data

US 2024/0189522 A1      Jun. 13, 2024

Related U.S. Application Data

(63) Continuation-in-part of application No. 17/205,280, filed on Mar. 18, 2021, now Pat. No. 11,925,749.

(51) Int. Cl.
*A61M 11/02*          (2006.01)

(52) U.S. Cl.
CPC .................................. *A61M 11/02* (2013.01)

(58) Field of Classification Search
CPC ............ A61M 15/025; A61M 15/0025; A61M 15/0086; A61M 15/08; A61M 15/085; A61M 2206/10; A61M 11/041; A61M 15/0028; A61M 15/0085; A61M 11/005; A61M 11/02; A61M 2210/0618

USPC ...................................................... 128/200.14
See application file for complete search history.

(56) References Cited

U.S. PATENT DOCUMENTS

| | | | |
|---|---|---|---|
| 4,747,820 A | 5/1988 | Hornlein et al. | |
| 6,257,232 B1 * | 7/2001 | Andersson | ........ A61M 15/0068 |
| | | | 128/203.15 |
| 6,810,875 B2 * | 11/2004 | Staniforth | ............ A61M 11/002 |
| | | | 128/200.14 |
| 8,377,009 B2 | 2/2013 | Sullivan et al. | |
| 8,656,909 B2 | 2/2014 | Godfrey et al. | |

(Continued)

FOREIGN PATENT DOCUMENTS

CN          212491195 U      2/2021

*Primary Examiner* — Elliot S Ruddie
(74) *Attorney, Agent, or Firm* — Brianna Schonenberg

(57) ABSTRACT

A pharmaceutical drug delivery device and method of preventing drying out and drooling of an ejection head for the drug delivery device. The device includes a device body; a fluid outlet nozzle attached to the device body; and a fluid jet ejection cartridge containing a liquid pharmaceutical drug disposed in the body. A fluid ejection head is attached to the fluid jet ejection cartridge and is in fluid flow communication with the fluid outlet nozzle. An elongate, serpentine air flow path disposed between an inner surface of the fluid outlet nozzle and a sealing material that is disposed between an outer surface of the fluid jet ejection cartridge and the inner surface of the fluid outlet nozzle, wherein the elongate, serpentine air flow path provides a reduced pressure differential adjacent to a surface of the ejection head upon use of the drug delivery device and provides a humidification zone.

13 Claims, 5 Drawing Sheets

(56)         References Cited

U.S. PATENT DOCUMENTS

| | | | |
|---|---|---|---|
| 9,492,625 B2 * | 11/2016 | Smyth | A61M 15/0028 |
| 9,636,430 B2 | 5/2017 | Gruenbacher et al. | |
| 10,668,230 B2 | 6/2020 | Giroux | |
| 10,814,079 B2 | 10/2020 | Francis et al. | |
| 2010/0024814 A1 | 2/2010 | Sugita et al. | |
| 2010/0083963 A1 | 4/2010 | Wharton et al. | |
| 2010/0276457 A1 | 11/2010 | Petit et al. | |
| 2011/0023869 A1 | 2/2011 | Djupesland | |
| 2011/0253752 A1 * | 10/2011 | Godfrey | A61M 11/08 |
| | | | 222/566 |
| 2013/0213397 A1 | 8/2013 | Curtis et al. | |
| 2014/0343494 A1 | 11/2014 | Hoekman et al. | |
| 2017/0203058 A1 | 7/2017 | Davidson et al. | |
| 2018/0369508 A1 | 12/2018 | Voon Hollen et al. | |
| 2019/0015855 A1 | 1/2019 | Hoxie et al. | |
| 2020/0179579 A1 | 6/2020 | Arnone et al. | |
| 2020/0353183 A1 | 11/2020 | Alt et al. | |

* cited by examiner

VENTING OF PHARMACEUTICAL DRUG DELIVERY DEVICE FOR AIR FLOW AND HUMIDITY CONTROL

RELATED APPLICATION

This application is a continuation-in-part of application Ser. No. 17/205,280, filed Mar. 18, 2021, now allowed.

TECHNICAL FIELD

The disclosure is directed to inhalation drug delivery systems and in particular to inhalation devices that have improved air flow and humidity control.

BACKGROUND AND SUMMARY

Nasal spray devices have become important methods for delivering drugs to patients. Such nasal spray devices are more convenient to use than the administration of drugs through IV or injection. Nasal spray devices also provide higher bioavailability of drugs compared to oral administration of drugs. The absorption of drugs through nasal spray devices is more rapid compared to the absorption of drugs administered orally since drugs delivered by nasal spray devices directly enter the blood stream making their effect more immediate.

FIG. 1 is a cross sectional view, not to scale, of anatomy of a nasal cavity 10 of a person. A portion of the brain 14 is shown above the nasal cavity 10. An olfactory bulb 14 is disposed between the brain 12 and a cribriform plate 16. An olfactory mucosa is below the cribriform plate 16. The nasal cavity also includes a superior turbinate 20, a middle turbinate 22, respiratory mucosa 24 and an inferior turbinate 26. Item 28 represents the palate. Injection of a pharmaceutical drug mist enters the nasal cavity 10 through the nostrils 30 and squamous mucosa 32. In order to achieve proper delivery of drugs to the blood stream using a nasal spray device, the drugs must be delivered to the respiratory mucosa which is highly vascularized. Two areas that are highly vascularized are the olfactory region and the respiratory region. The respiratory region contains turbinates which increase the surface area available for drug absorption.

Conventional methods for delivering drugs via the nasal cavity include medicine droppers, multi-spray bottles with spray tips, single-dose syringes with spray tips, and dry powder systems. Accordingly, conventional drug delivery devices are typically designed to deliver a specific drug to a nasal cavity and each device cannot be adapted for delivering a wide range of drugs via a nasal cavity route. Many of the conventional methods for nasal drug delivery rely on pressurized containers to inject a mist of fluid into the nasal cavity. Accordingly, the drug delivery devices are typically designed for a specific drug and cannot be adapted to administer a different drug.

Despite the availability of a variety of devices for delivering drugs via a nasal cavity route, there remains a need for a nasal drug delivery device that can be adapted to deliver a variety of drugs. One such device is an on-demand fluid jet delivery device. Conventional fluid jet delivery devices operate to eject fluid to a substrate under ambient atmospheric pressure. However, when a nozzle of a nasal applicator is used, the nozzle is inserted into one nostril of a user which closes off the nostril to the ambient atmosphere. When the user breathes in, a low pressure area is generated in the nozzle of the device. If the nasal applicator uses a fluid jet delivery ejection head attached to a fluid cartridge, the low pressure will provide a pressure differential that will cause fluid inside of fluid cartridge to drool out of the ejection head and puddle on the surface thereof. Such fluid puddling interferes with fluid jetting from the ejection head and delivery of a precise amount of pharmaceutical drug to the user.

Another problem associated with using a fluid jet ejector device to administer drugs to a user's nasal cavity is that fluid may dry out on the ejection head between uses and interfere with fluid ejected through fluid nozzles on the ejection head causing misdirection of fluid and misfiring of fluid ejectors. Accordingly, what is needed is an improved nasal applicator that is designed to prevent drooling of fluid from a fluid cartridge having a fluid jet delivery device to eject fluid into a nasal cavity of a user. The device must also prevent fluid from drying out on the ejection head between uses of the device.

In view of the foregoing an embodiments of the disclosure provide a pharmaceutical drug delivery device and method of preventing drying out and drooling of an ejection head for the drug delivery device. The device includes a drug delivery device body; a fluid outlet nozzle attached to the drug delivery device body; and a fluid jet ejection cartridge containing a liquid pharmaceutical drug disposed in the drug delivery device body. A fluid ejection head is attached to the fluid jet ejection cartridge and the fluid ejection head is in fluid flow communication with the fluid outlet nozzle. An elongate, serpentine air flow path is provided between an inner surface of the fluid outlet nozzle and a sealing material that is disposed between an outer surface of the fluid jet ejection cartridge and the inner surface of the fluid outlet nozzle, wherein the elongate, serpentine air flow path provides a reduced pressure differential adjacent to a surface of the fluid ejection head upon use of the drug delivery device and provides a humidification zone.

In one embodiment, there is provided a method for reducing a pressure differential on a fluid jet ejection head for a nasal spray device. The method includes providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge. A sealing material is inserted between an outer surface of the fluid jet ejection cartridge and an inner surface of the fluid outlet nozzle. The inner surface of the fluid outlet nozzle contains an elongate, serpentine air flow path between the inner surface of the fluid outlet nozzle and an outer surface of the sealing material to provide a reduced pressure differential adjacent to a surface of the fluid ejection head upon use of the drug delivery device. The nasal spray device is activated while flowing air through the drug delivery device body and the elongate, serpentine air flow path when the fluid outlet nozzle is inserted into the nasal passage of a user thereby preventing fluid from drooling from the fluid ejection head.

In another embodiment, there is provided a method for preventing a surface of a fluid jet ejection head for a nasal spray device from drying out between uses. The method includes providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge. A sealing material is inserted between an outer surface of the fluid jet ejection cartridge and an inner surface of the fluid outlet nozzle. The inner surface of the fluid outlet nozzle contains an elongate, serpentine air flow path between the inner surface of the fluid outlet nozzle and an outer surface of the sealing material to provide a humidification zone in the drug delivery device adjacent to a surface of the fluid ejection head between uses of the drug delivery device. The fluid outlet nozzle is plugged with a cap to prevent drying out of the surface of the fluid jet ejection head.

In another embodiment, the elongate, serpentine air flow path has a length to cross-sectional area ratio of about 30:1 to about 100:1.

In some embodiments, the elongate, serpentine air flow path is a spiral path formed in the inner surface of the fluid outlet nozzle.

In some embodiments, the reduced pressure differential is provided between the outer surface of the fluid jet ejection cartridge and the serpentine air flow path between the outer surface of the sealing material and the inner surface of the fluid outlet nozzle.

In some embodiments, a plug is provided to cap off the fluid outlet nozzle and create the humidification zone in the drug delivery device between uses.

In some embodiments, the humidification zone is provided between outer surface of the fluid jet ejection cartridge and the serpentine air flow path between the outer surface of the sealing material and the inner surface of the fluid outlet nozzle.

An advantage of disclosed embodiments is that a single sealing material in combination with a serpentine path molded into an inner surface of the fluid outlet nozzle can be used to provide both reduced pressure differential on a jet ejection head during use of the pharmaceutical device and can provide a humidification zone in the device when capped to prevent the ejection head from drying out.

DETAILED DESCRIPTION

Figure 1:
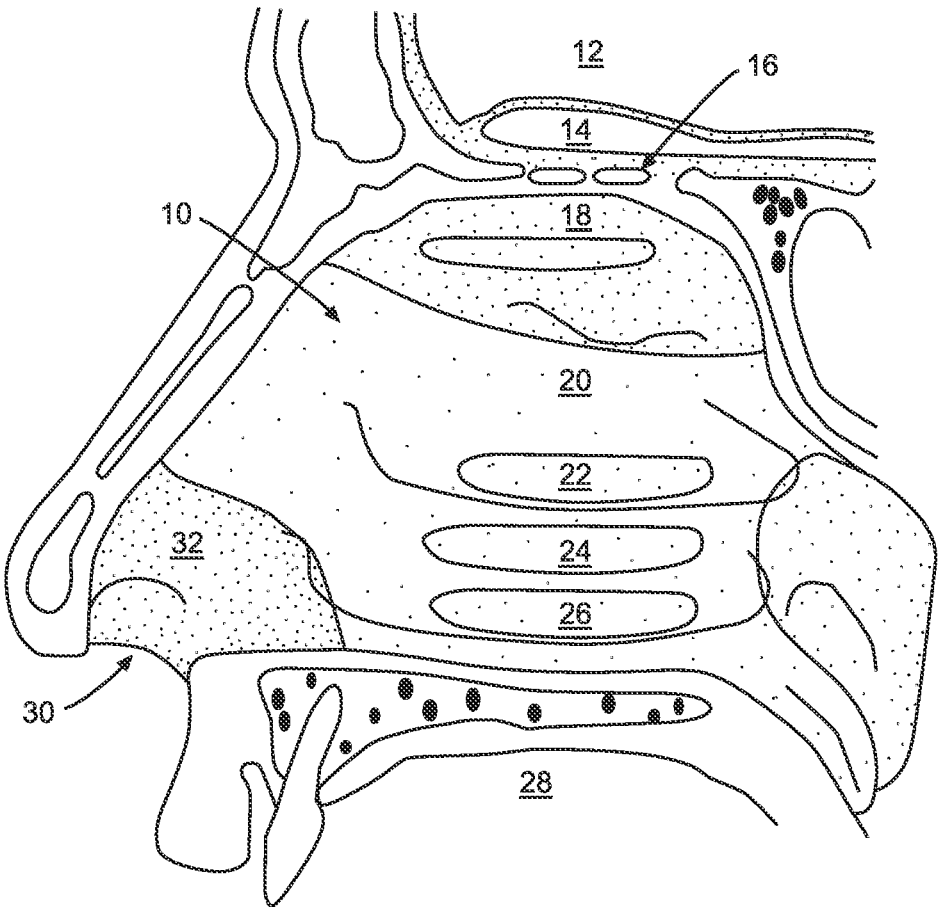
FIG. 1 is a cross-sectional representation, not to scale, of a portion of a nasal cavity and scull of a person.
Figure 2:
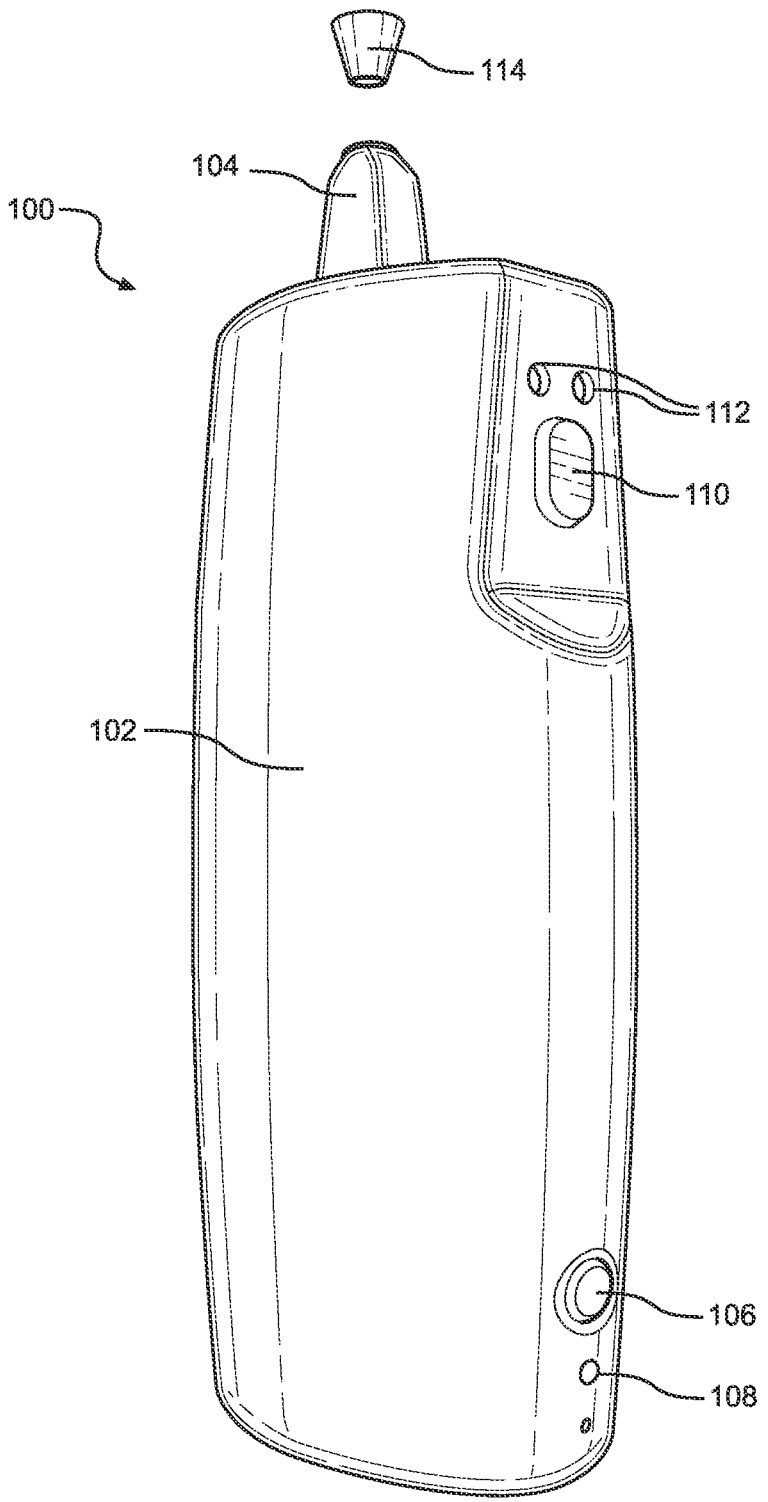
FIG. 2 is a perspective view, not to scale of a pharmaceutical drug delivery device according to an embodiment of the disclosure.

An illustration of a pharmaceutical drug delivery device 100 is illustrated in FIG. 2. The device includes a drug delivery device body 102, having a fluid outlet nozzle 104 attached to the drug delivery device body 102. A power button 106 is provided to activate the drug delivery device as indicated by an LED 108. During use of the device 100, a dispense button 110 is pressed and fluid delivery is indicated by LED's 112. When not in use, a plug 114 may be inserted into the device 100 to prevent fluid from drying out on a fluid jet ejection head used to deliver the pharmaceutical drug to a user. The drug delivery device body 102 also contains a power source and a controller for controlling the ejection of fluid from the fluid jet ejection head.

Figure 3:
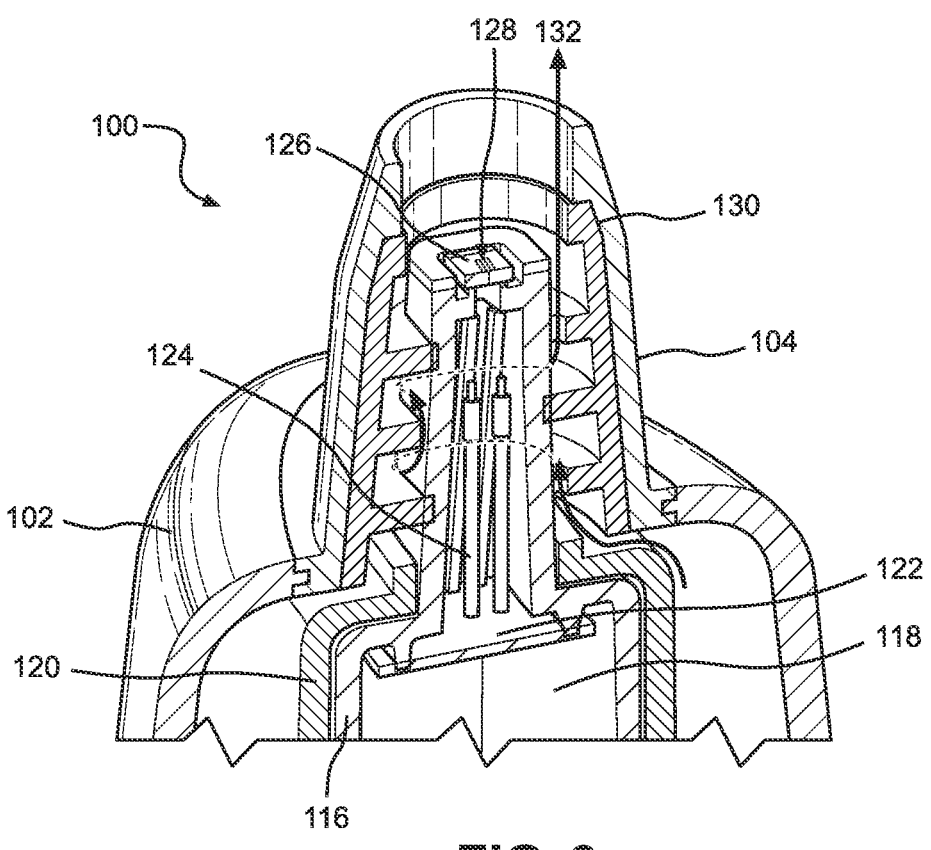
FIG. 3 is a partial perspective, cross-sectional view, not to scale, of the drug delivery device of FIG. 2 containing a sealing material according to a first embodiment of the disclosure.

With reference to FIG. 3, a cross-sectional perspective view of a portion of the drug delivery device 100 is illustrated. The drug delivery device 100 includes the drug delivery device body 102 for holding a fluid jet ejection cartridge 116 containing a pharmaceutical fluid 118 in a cartridge holder 120. A fluid filter 122 is disposed in the cartridge 116 to filter the fluid flowing through filter tower structures 124 to a fluid jet eject ejection head 126. In some embodiments, the fluid cartridge 116 may also contain a backpressure control device such as a bladder or foam for inducing a backpressure on the fluid jet ejection head 126. The fluid jet ejection head 126 may be selected from any of the conventional types of fluid jet ejection heads, including but not limited to, thermal jet ejection heads, bubble jet ejection heads, piezoelectric jet ejection heads, and the like. Each of the foregoing ejection heads can produce a spray of fluid on demand.

As set forth above, when the fluid outlet nozzle 104 is inserted into the nostril 30 of a user, and the user inhales, a low pressure area is formed adjacent to an exposed surface 128 of the ejection head 126. This low pressure area creates a "pressure differential" between the surface 128 of the ejection head 126 and the fluid in the cartridge 116. The pressure differential can cause unwanted flow or drooling of fluid from the ejection head 126. Accordingly, in order to reduce the pressure differential adjacent to the surface 128 of the ejection head 126, a sealing material 130 containing a serpentine air flow path 132, is provided in the fluid outlet nozzle 104 surrounding the cartridge 116. In one embodiment, the sealing material 130 contains alternating notches 134 that are in fluid flow communication with adjacent air chambers 136 so that a serpentine path through the sealing material 130 is provided.

The sealing material for use with the device 100 may be selected from a wide variety of sulfur-free resilient materials such as natural or synthetic rubber, and thermoplastic or thermoset elastomers having a shore A durometer of less than about 60 that are compatible with the fluids being ejected from the ejection head 126. Examples of such materials include, but are not limited to natural rubber, EPDM rubber, and a dynamically vulcanized alloy consisting mostly of fully cured EPDM rubber particles encapsulated in a polypropylene (PP) matrix, available from ExxonMobil under the tradename SANTOPRENE. The sealing material 130 can be molded and shaped to provide the serpentine air flow path 132 therein and can provide a seal between the fluid jet ejection cartridge 116 and the fluid outlet nozzle 104. It will be appreciated that the drug delivery device body 102 of the device 100 is not air-tight and thus provides inlet air flows from a variety of locations such as from the buttons 106 and 110 and any opening provided for inserting the fluid jet ejection cartridge 116 into the drug delivery device body 102.

Figure 4:
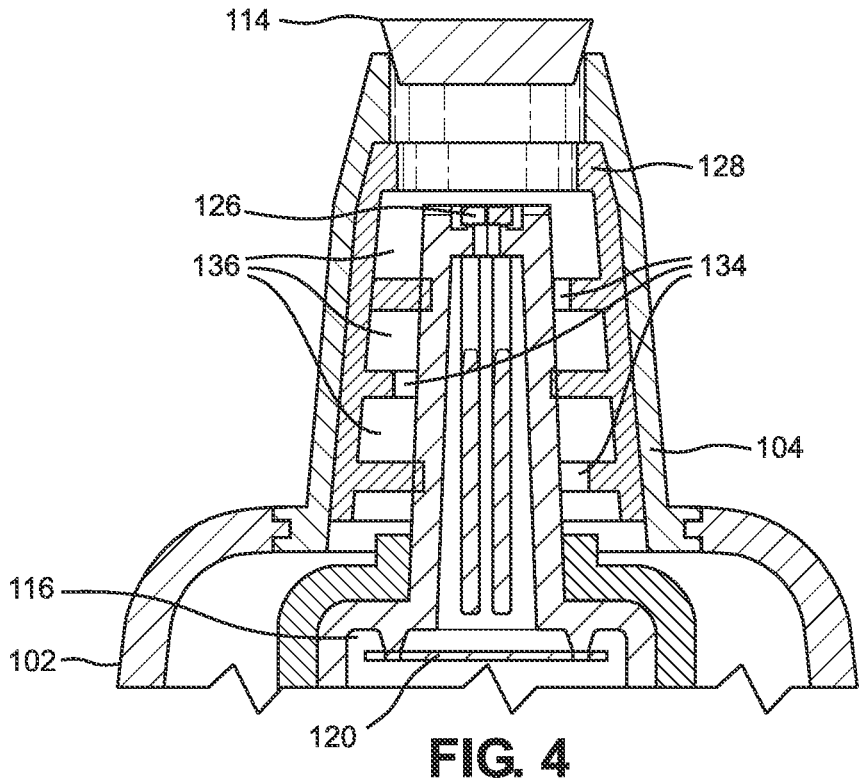
FIG. 4 is a partial cross-sectional view, not to scale, of the sealing material in the fluid outlet nozzle of the device of FIG. 3.

When the fluid outlet nozzle 104 is capped with a plug 114 as shown in FIG. 4, the chambers 136 provide areas for holding humid air so that any fluid on the surface 128 of the ejection head 126 is less likely to dry out between uses of the device 100. Thus chambers 136 provide humidification zones in the fluid outlet nozzle 104 of the device 100 when capped.

Figure 5:
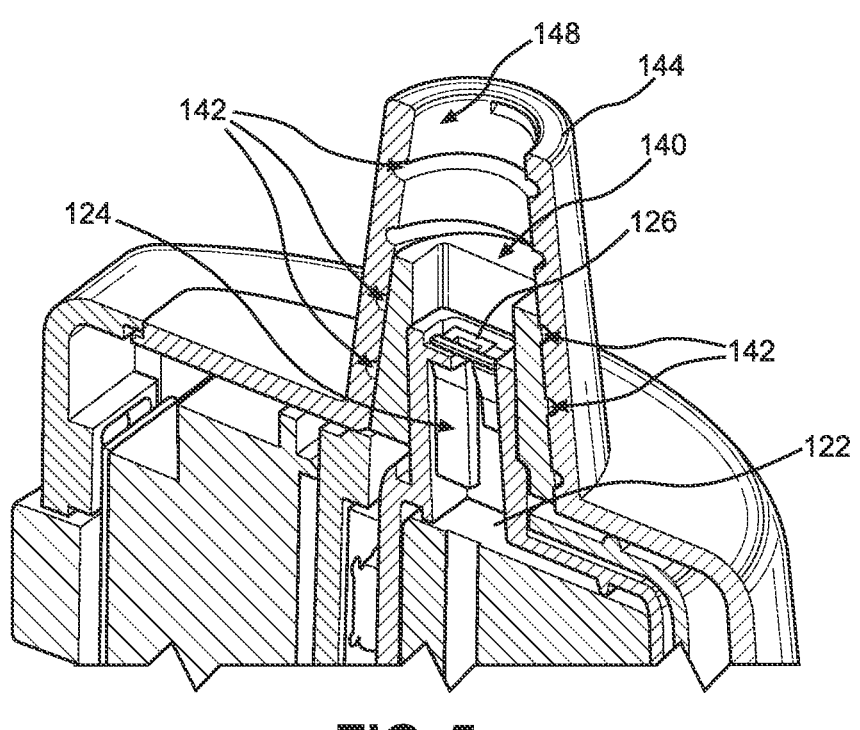
FIGS. 5-6 are partial perspective, cross-sectional views, not to scale, of the drug delivery device of FIG. 2 containing a serpentine flow path formed in an outlet nozzle according to a second embodiment of the disclosure.
Figure 6:
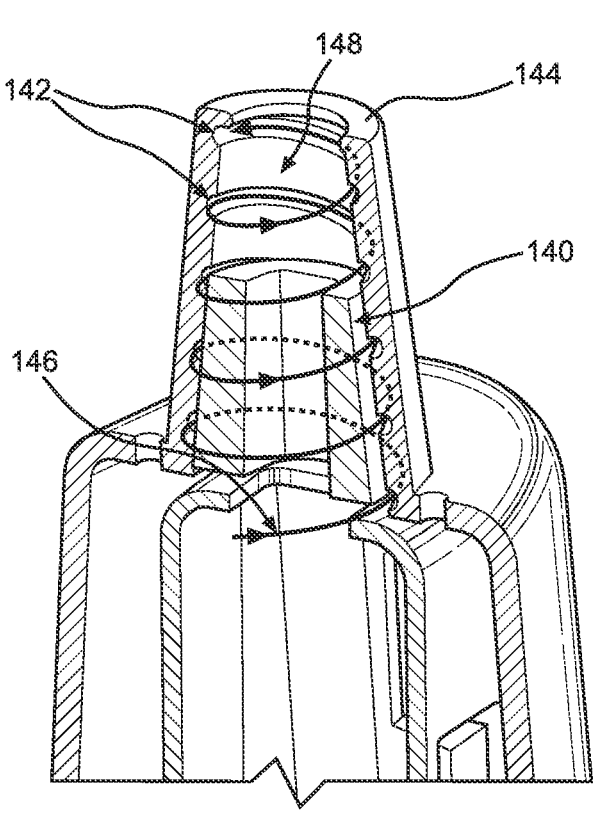
Figure 7:
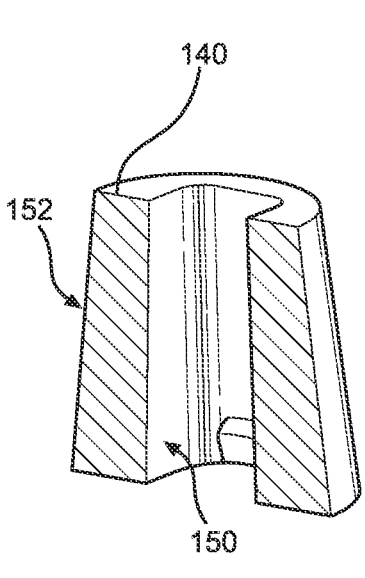
FIG. 7 is a perspective, cross-sectional view, of a sealing material for the outlet nozzle of FIGS. 5-6.

FIGS. 5-7 provide details of another embodiment of a sealing material 140 and air flow path 142 through a fluid outlet nozzle 144 according to another embodiment of the disclosure. In the embodiment of FIGS. 5-6, the air flow path 142 is a spiral path indicated by arrow 146 (FIG. 6) formed or molded into an interior surface 148 of the fluid outlet nozzle 144 thereby providing a serpentine air flow path 142 between the sealing material 140 and the inner surface 148 of the fluid outlet nozzle 144. As shown in FIG. 7, both an inner surface 150 and an outer surface 152 of the sealing material 140 are smooth. Accordingly, as shown in FIG. 5, when inserted into the outlet nozzle 144, the sealing material 140 may prevent stray air currents in the vicinity of the ejection head 126 by fitting snuggly around the filter tower structure 124 as compared to the serpentine flow path shown in FIGS. 3-4.

Figure 8:
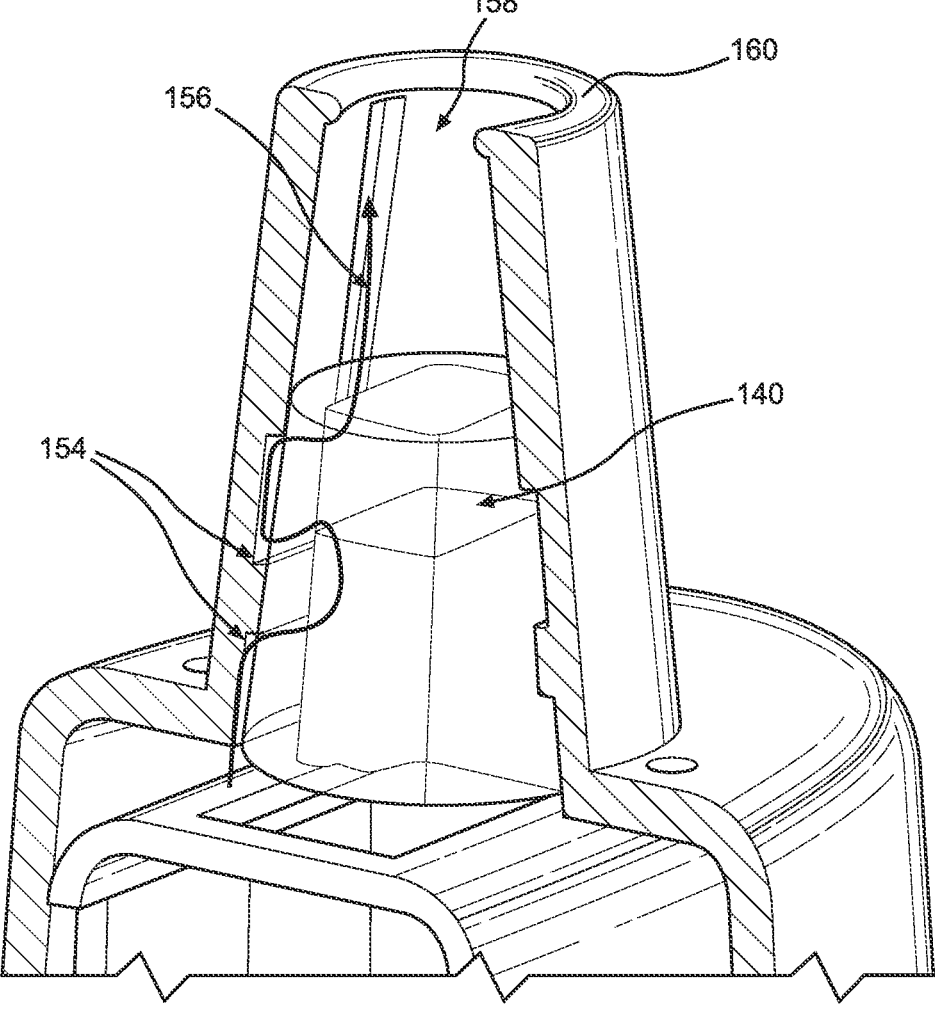
FIG. 8 is partial perspective, cross-sectional view, not to scale, of the drug delivery device of FIG. 2 containing a serpentine flow path formed in an outlet nozzle according to a third embodiment of the disclosure.

FIG. 8 provides yet another embodiment of the disclosure. In FIG. 8, one or more serpentine flow paths 154, indicated by arrow 156, are a zig-zag flow paths 154 formed or molded into an interior surface 158 of the fluid outlet nozzle 160 between the sealing material 140 and the inner surface 158 of the fluid outlet nozzle 160. At least two serpentine flow paths 154 are molded or formed into the interior surface 158 of the fluid outlet nozzle on opposite sides of the fluid outlet nozzle 160. As described above, when the sealing material 140 is inserted into the outlet nozzle to provide the serpentine flow paths 154 between the sealing material and the inner surface of the outlet nozzle 160, stray air currents in the vicinity of the ejection head 126 may be prevented. In some embodiments described above, the serpentine air flow path 142 has a length to area ratio ranging from about 30:1 to about 100:1, such as from about 35:1 to about 60:1.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

6

What is claimed is:

1. A pharmaceutical drug delivery device comprising:
   a drug delivery device body;
   a fluid outlet nozzle attached to the drug delivery device body;
   a fluid jet ejection cartridge containing a liquid pharmaceutical drug is disposed in the drug delivery device body, wherein a fluid ejection head is attached to the fluid jet ejection cartridge and the fluid ejection head is in fluid flow communication with the fluid outlet nozzle; and
   an elongate, serpentine air flow path disposed between an inner surface of the fluid outlet nozzle and a sealing material that is disposed between an outer surface of the fluid jet ejection cartridge and the inner surface of the fluid outlet nozzle, wherein the elongate, serpentine air flow path provides a reduced pressure differential adjacent to a surface of the fluid ejection head upon use of the drug delivery device and provides a humidification zone.

2. The pharmaceutical drug delivery device of claim 1, wherein the elongate, serpentine air flow path has a length to cross-sectional area ratio of greater than 30:1 to about 100:1.

3. The pharmaceutical drug delivery device of claim 1, wherein the elongate, serpentine air flow path comprises a spiral path formed in the inner surface of the fluid outlet nozzle.

4. The pharmaceutical drug delivery device of claim 1, wherein the elongate, serpentine air flow path comprises multiple zig-zag flow paths formed in the inner surface of the fluid outlet nozzle.

5. The pharmaceutical drug delivery device of claim 1, further comprising a plug to cap off the fluid outlet nozzle and create the humidification zone in the drug delivery device between uses.

6. A method for reducing a pressure differential on a fluid jet ejection head for a nasal spray device, the method comprising:
   providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge;
   inserting a sealing material between an outer surface of the fluid jet ejection cartridge and an inner surface of the fluid outlet nozzle, wherein the inner surface of the fluid outlet nozzle contains an elongate, serpentine air flow path between the inner surface of the fluid outlet nozzle and an outer surface of the sealing material to provide a reduced pressure differential adjacent to a surface of the fluid ejection head upon use of the drug delivery device; and
   activating the nasal spray device while flowing air through the drug delivery device body and the elongate, serpentine air flow path when the fluid outlet nozzle is inserted into the nasal passage of a user thereby preventing fluid from drooling from the fluid ejection head.

7. The method of claim 6, wherein the elongate, serpentine air flow path has a length to cross-sectional area ratio of about 30:1 to about 100:1.

8. The method of claim 6, wherein the reduced pressure differential is provided by a spiral path molded into an inner surface of the fluid outlet nozzle.

9. The method of claim 8, wherein the reduced pressure differential is provided between the outer surface of the fluid jet ejection cartridge and the serpentine air flow path between the outer surface of the sealing material and the inner surface of the fluid outlet nozzle.

10. The method of claim 6, wherein the reduced pressure differential is provided by one or more zig-zag flow paths molded into an inner surface of the fluid outlet nozzle.

11. A method for preventing a surface of a fluid jet ejection head for a nasal spray device from drying out between uses, the method comprising:

providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge;

inserting a sealing material between an outer surface of the fluid jet ejection cartridge and an inner surface of the fluid outlet nozzle, wherein the inner surface of the fluid outlet nozzle contains an elongate, serpentine air flow path between the inner surface of the fluid outlet nozzle and an outer surface of the sealing material to provide a humidification zone in the drug delivery device adjacent to a surface of the fluid ejection head between uses of the drug delivery device; and plugging the fluid outlet nozzle with a cap to prevent drying out of the surface of the fluid jet ejection head.

12. The method of claim 11, wherein the elongate, serpentine air flow path has a length to cross-sectional area ratio of about 30:1 to about 100:1.

13. The method of claim 12, wherein the humidification zone is provided between outer surface of the fluid jet ejection cartridge and the serpentine air flow path between the outer surface of the sealing material and the inner surface of the fluid outlet nozzle.

* * * * *